(12) United States Patent
Melville

(10) Patent No.: US 8,096,943 B2
(45) Date of Patent: Jan. 17, 2012

(54) FLEXIBLE ENDOSCOPE TIP BENDING MECHANISM USING OPTICAL FIBER AS COMPRESSION MEMBER

(75) Inventor: Charles David Melville, Issaquah, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 768 days.

(21) Appl. No.: 11/566,597

(22) Filed: Dec. 4, 2006

(65) Prior Publication Data

US 2008/0132762 A1 Jun. 5, 2008

(51) Int. Cl.
*A61B 1/00* (2006.01)

(52) U.S. Cl. .......................... 600/146; 600/139; 600/149

(58) Field of Classification Search .................. 600/139, 600/140–144, 146, 149, 114, 150
See application file for complete search history.

(56) References Cited

U.S. PATENT DOCUMENTS

| | | | |
|---|---|---|---|
| 4,530,568 A * | 7/1985 | Haduch et al. ................ 385/118 |
| 4,686,963 A | 8/1987 | Cohen et al. ...................... 128/4 |
| 4,688,555 A | 8/1987 | Wardle ............................... 128/4 |
| 4,695,163 A | 9/1987 | Schachar ...................... 356/369 |
| 4,745,908 A * | 5/1988 | Wardle ........................... 600/139 |
| 4,748,969 A * | 6/1988 | Wardle ........................... 600/150 |
| 4,758,222 A | 7/1988 | McCoy ............................ 604/95 |
| 4,762,118 A | 8/1988 | Lia et al. ........................... 128/4 |
| 4,870,951 A * | 10/1989 | Suzuki ........................... 600/130 |
| 4,976,688 A * | 12/1990 | Rosenblum ................ 604/95.04 |
| 4,979,496 A * | 12/1990 | Komi ............................. 600/113 |
| 4,983,165 A | 1/1991 | Loiterman ................... 604/95.03 |
| 5,257,618 A * | 11/1993 | Kondo ........................... 600/150 |
| 5,381,782 A | 1/1995 | DeLaRama et al. ............... 128/4 |
| 5,507,725 A | 4/1996 | Savage et al. ............... 604/95.04 |
| 5,512,035 A | 4/1996 | Konstorum et al. .......... 600/146 |
| 5,549,542 A | 8/1996 | Kovalcheck ................... 600/146 |
| 6,246,914 B1 | 6/2001 | de la Rama et al. .......... 607/122 |
| 6,458,076 B1 * | 10/2002 | Pruitt ............................. 600/146 |

(Continued)

FOREIGN PATENT DOCUMENTS

EP 0 713 672 5/1996

(Continued)

OTHER PUBLICATIONS

Finci, L; Meier, B; Steffenino, G; Rutishauser, W; "Tandem balloon catheter for coronary angioplasty." Cathet CardioVasc Diagn, vol. 12, No. 6, pp. 421-425.

(Continued)

*Primary Examiner* — Anhtuan Nguyen
*Assistant Examiner* — Alireza Nia

(57) ABSTRACT

A flexible endoscope includes an elongate flexible extrusion. A central lumen extends longitudinally through the center of the extrusion, and a plurality of other longitudinally extending lumens are spaced around the central lumen. An optical fiber is inserted within the central lumen and is coupled to its inner surface. This optical fiber serves as a compression member and conveys light through the flexible endoscope. A first pair of tension members extend through lumens on opposite sides of the central lumen. Applying a tension force to one of these tension members causes a distal tip of the flexible endoscope to bend in a first direction, while applying a tension force to the opposite tension member causes the distal tip to bend in an opposite direction. Providing a second pair of tension members in lumens disposed orthogonal to the first pair enables bending of the distal tip relative to orthogonal axes.

21 Claims, 5 Drawing Sheets

U.S. PATENT DOCUMENTS

| | | | |
|---|---|---|---|
| 6,461,337 B1 | 10/2002 | Minotti et al. | 604/264 |
| 6,858,005 B2 | 2/2005 | Ohline et al. | 600/141 |
| 6,932,829 B2 | 8/2005 | Majercak | 606/198 |
| 6,975,898 B2 | 12/2005 | Seibel et al. | 600/473 |
| 7,395,116 B2 * | 7/2008 | Mehdizadeh et al. | 607/37 |
| 2001/0034547 A1 | 10/2001 | Hall et al. | 623/1.11 |
| 2002/0100484 A1 | 8/2002 | Hall et al. | 128/898 |
| 2002/0142119 A1 | 10/2002 | Seward et al. | 428/36.9 |
| 2003/0009189 A1 | 1/2003 | Gilson et al. | 606/200 |
| 2003/0236564 A1 | 12/2003 | Majercak | 623/1.11 |
| 2004/0118415 A1 | 6/2004 | Hall et al. | 128/898 |
| 2004/0147827 A1 | 7/2004 | Bowe | 600/374 |
| 2004/0243227 A1 | 12/2004 | Starksen et al. | 623/2.11 |
| 2005/0085693 A1 | 4/2005 | Belson et al. | 600/146 |
| 2005/0171592 A1 | 8/2005 | Majercak | 623/1.11 |
| 2005/0228290 A1 | 10/2005 | Borovsky et al. | 600/466 |
| 2005/0250983 A1 | 11/2005 | Tremaglio et al. | 600/101 |
| 2005/0272975 A1 | 12/2005 | McWeeney et al. | 600/113 |
| 2006/0030753 A1 | 2/2006 | Boutillette et al. | 600/146 |
| 2006/0100480 A1 | 5/2006 | Ewers et al. | 600/114 |
| 2006/0149134 A1 | 7/2006 | Soper et al. | 600/182 |
| 2006/0252993 A1 | 11/2006 | Freed et al. | 600/146 |
| 2007/0270650 A1 | 11/2007 | Eno et al. | 600/145 |

FOREIGN PATENT DOCUMENTS

| | | |
|---|---|---|
| EP | 0 520 338 | 11/1996 |
| EP | 0 712 032 | 12/2001 |
| WO | WO 93/20742 | 10/1993 |
| WO | WO 98/43530 | 10/1998 |
| WO | WO 01/97902 | 12/2001 |

OTHER PUBLICATIONS

Yamamoto, H; Sekine, Y; Sato, Y; Higashizawa, T; Miyata, T; Iino, S; Ido, K; Sugano, K; "Total enteroscopy with a nonsurgical steerable double-balloon method." Gatrointest Endosc, vol. 53, No. 2, pp. 216-220. Feb. 2001.

Yoon, W. Jong, Reinhall, Per G., and Seibel, Eric J. "Analysis of Electro Active Polymer Bending: A Component in a Low Cost Ultrathin Scanning Endoscope," pp. 1-26. Published Jul. 2006. University of Washington, Seattle, WA.

* cited by examiner

FLEXIBLE ENDOSCOPE TIP BENDING MECHANISM USING OPTICAL FIBER AS COMPRESSION MEMBER

BACKGROUND

Flexible endoscopes have become increasingly preferred as the instrument of choice for performing certain types of surgical procedures, performing certain diagnostic procedures, or rendering therapy to internal sites within a patient's body. Since the endoscope can be inserted through a natural body opening or through a relatively small transcutaneous incision and advanced to the site where the medical procedure is to be performed, the use of an endoscope exposes the patient to much less trauma and risk of infection than a conventional surgical technique that would otherwise be required to access the internal site. The use of a flexible endoscope is so minimally invasive that some medical procedures can be done in a clinic with the device, and the patient released within an hour or two after a procedure has been completed.

Depending upon the internal site where a medical procedure will be performed with a flexible endoscope, it may be necessary to remotely bend the distal tip of the endoscope, for example, to facilitate advancing the endoscope through a curving body lumen or to position the distal tip at a desired orientation to implement the medical procedure with the endoscope. Although the term "flexible" endoscope indicates that the endoscope is not rigid, some mechanism must be provided to actually bend the flexible distal portion of the endoscope in a desired direction and by a required amount. The conventional approach for bending the distal tip employs wires that extend coaxially along the flexible endoscope, so that when the proximal end of a wire is pulled relative to the shaft of the flexible endoscope, the distal end bends in the direction of that wire. A wire running down the opposite side of the flexible endoscope is then pulled to straighten the distal tip or bend it in the opposite direction. If four of these coaxial wires extend down the length of the flexible endoscope to enable bending of its distal tip in each direction about orthogonal X and Y axes, the wires add substantially to the diameter of the device. However, there is a significant advantage in using a flexible endoscope having a diameter on the order of 1 mm or less. But such a small diameter flexible endoscope can generally not be achieved if the conventional coaxial bending wire arrangement is used to bend the distal tip. Accordingly, a different approach is required that provides the desired small diameter, yet enables the distal tip to be selectively bent in any of four orthogonally different directions.

SUMMARY

To enable endoscopic devices that continue to become ever smaller to perform the same functions as more conventional endoscopes, it is important to recognize that elements of their design must have multiple functions. In the case of a small flexible endoscope, an exemplary design using an optical fiber as the main light conduit from the proximal end to the distal tip can be used. One interesting mechanical property of an optical fiber, which made of fused silica, is its mechanical strength. The compressive strength of stainless steel is about 95,000 PSI. In contrast, fused silica has a compressive strength of about 160,000 PSI, which is about 1.6 times the compressive strength of stainless steel. A 125-micron diameter optical fiber has over 3 pounds of compressive strength, which is more than enough for enabling the distal tip bending function required. A coaxial, "inside out design" is employed to complete the device.

More specifically, one exemplary embodiment of a flexible endoscope having a distal tip that can be selectively bent includes a flexible extrusion that is elongate, extending between a proximal end and a distal end. A plurality of lumens are formed within the flexible extrusion. At least two lumens of the plurality of lumens are disposed on opposite sides of, and radially outward of a central lumen within the flexible extrusion. At least a pair of tension members each extend proximally through a different one of the plurality of lumens from an attachment point where the tension member is connected to the flexible extrusion. Each attachment point is disposed adjacent to the distal tip of the flexible extrusion. The tension members are free to slide longitudinally within the lumens proximal of the attachment points. An optical fiber that conveys light is disposed within the central lumen and is bonded to the flexible extrusion. The optical fiber serves as a compression member so that when tension is applied to a first tension member relative to the optical fiber, the distal tip of the flexible endoscope is bent in a first direction. Similarly, when tension is applied to a second tension member that is disposed generally diametrically opposite the first tension member, the flexible endoscope is bent in a second direction that is opposite to the first direction. The distal tip of the flexible endoscope can thus be selectively caused to bend in at least two opposite directions.

If two pairs of lumens are used for conveying tension members and are disposed at cardinal locations around the central lumen, tension can be applied to selected tension members to cause the distal tip to bend relative to two orthogonal axes. The tension members can be formed of KEVLAR™ (i.e., of fibers comprising long, highly oriented molecular chains of poly-paraphenylene terephthalamide), glass fibers, carbon fibers, or metal, such as steel wire. The flexible extrusion can be formed of a material selected for a characteristic low coefficient of friction, such as TEFLON™ (i.e., polytetrafluoroethylene), so that the tension fibers can readily slide within the lumens through which they pass.

In at least some embodiments, the plurality of lumens extend helically around the central lumen. By passing the tension member through such helical lumens, the relative length of the tension members on opposite sides of the central lumen (i.e., on an inside of a bend and on the outside of the bend) remains generally the same when the distal tip is bent.

At least some embodiments include only non-metallic tension members that are selected for a characteristic high tensile strength. From just before the distal tip to the proximal end of the flexible enclosure, the lumens through which the tension members pass and which are disposed on opposite sides of the central lumen can be diametrically closer together than proximate to the distal tip, to provide more of a moment arm for bending the distal tip.

Another aspect of this invention is directed to a method for enabling a distal tip of a flexible endoscope to be selectively bent. The method includes steps that are generally consistent with the functions of the elements of the flexible endoscope discussed above.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

DESCRIPTION

Figure 1A:
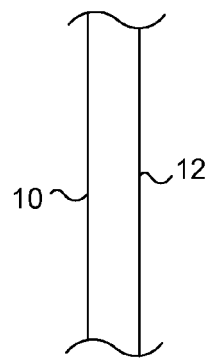
FIGS. 1A and 1B are schematic illustrations of two members, showing how the effective relative path lengths of the members change as they are bent from a parallel configuration (FIG. 1A) to a bent configuration (FIG. 1B)

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

Figure 1B:
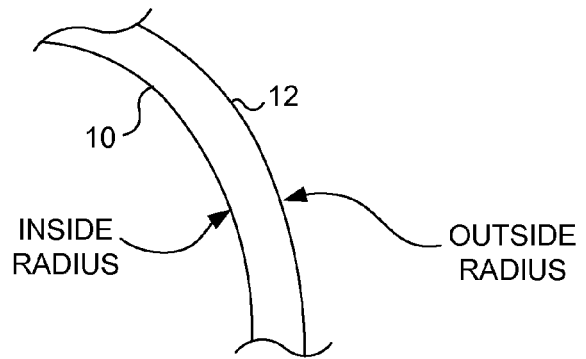

To minimize accidental tip bending while transmitting the compression and tension forces to the distal end, the members' relative path lengths should not change when sections along the length of the flexible endoscope are bent. FIGS. 1A and 1B are schematic drawings illustrating that when two parallel members 10 and 12 are bent, the radius of curvature is less for the inside member than the outside member. Since the path length for the inside member around a curve is less than for the outside member, the inside member is relatively longer compared to the outside member. Accordingly, it can be seen in FIG. 1B that the effective path lengths of the two members, relative to each other, have changed, as a result of the bending of the two members.

Figure 2:
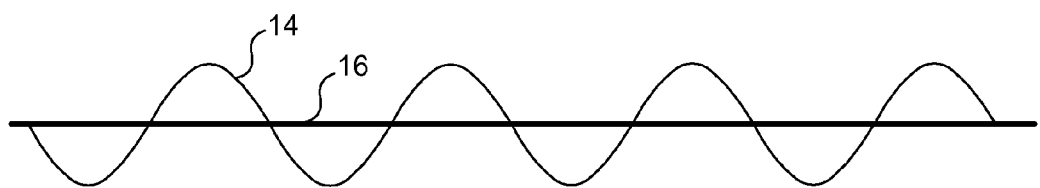
FIG. 2 is a schematic representation of two members, including a helically coiled tension member and an internal compression member.
Figure 3:
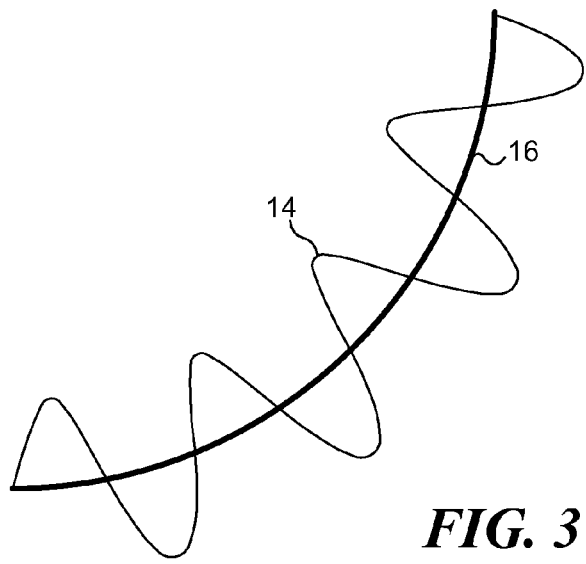
FIG. 3 is a schematic representation of the two members of FIG. 2, illustrating how bending the two members does not generally change their relative lengths.

To avoid the change in path length when such members are bent requires a modification to the parallel member configuration illustrated in FIG. 1A. Specifically, if a member 14 is wrapped around a member 16 in a helix, as shown in FIG. 2, then when both members are bent, as indicated in FIG. 3, the average length of both members will remain almost the same.

Figure 4:
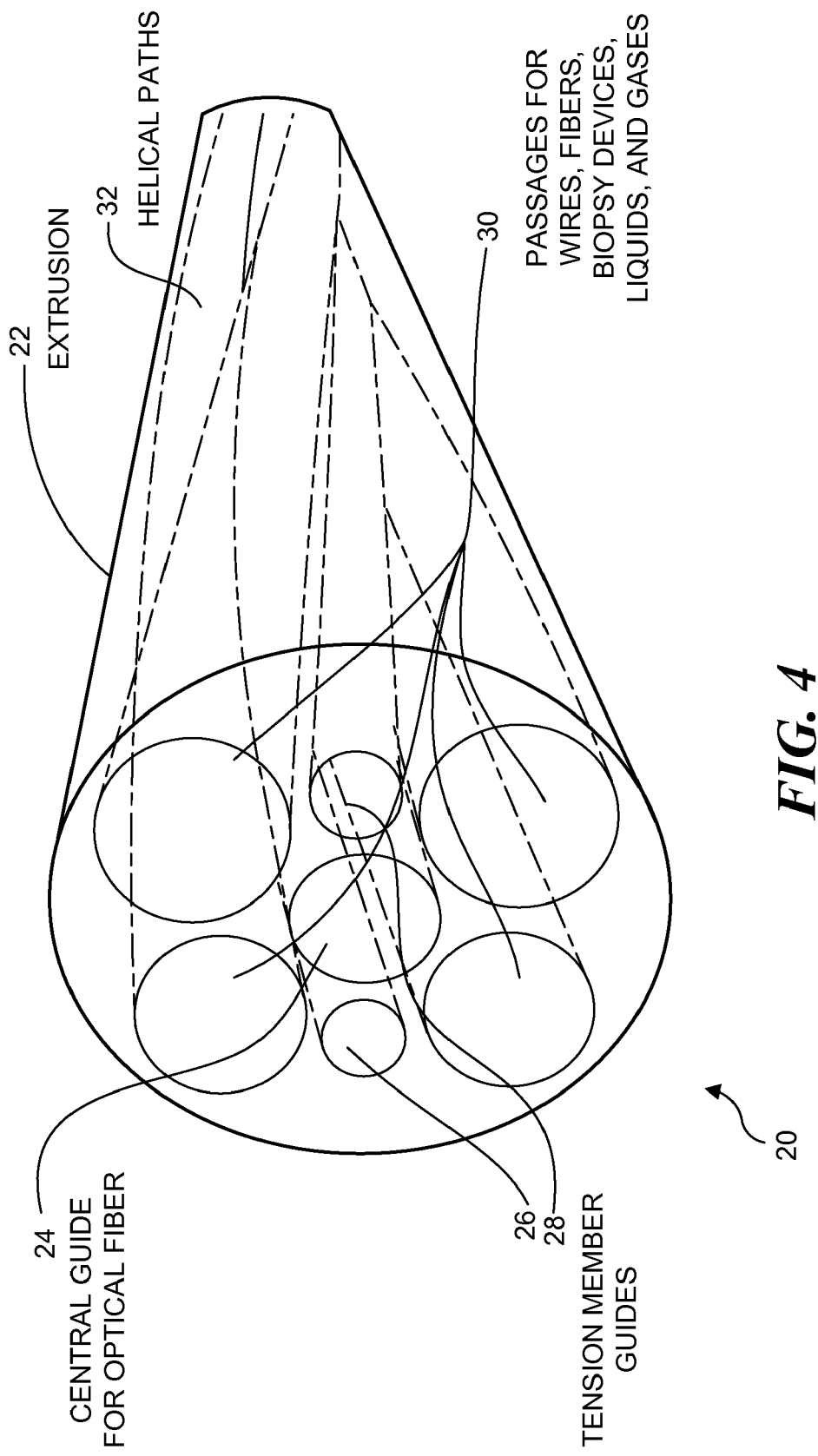
FIG. 4 is a cross-sectional perspective view of a portion of an extrusion having a plurality of helical lumens, including two lumens through which tension members extend helically and longitudinally, distributed about a central lumen, for use in a small diameter flexible endoscope having a bendable distal tip.

If the inner member is employed as a compression member, and the outer helical member serves as a tension member for use in bending the distal tip of a flexible endoscope, a guide will be required to retain the outer tension member in the helical path so that it can provide tension in regard to the compression member. FIG. 4 illustrates how such a helical guide 20 can be made from an extrusion 22 having a central lumen 24 that extends longitudinally down the center of the extrusion, and a plurality of lumens 26 and 28 extending longitudinally on diametrically opposite sides of the central lumen. Lumen 26 is provided to convey one of two tension members (neither shown in this Figure), and lumen 28 is provided to convey the other. The pitch of the helix of lumens 24 and 26 is about 1 cm in this exemplary embodiment.

While not shown in FIG. 4, central lumen 24 is provided to guide an optical fiber between proximal and distal ends of the extrusion. The optical fiber transmits light and also serves as the compression member when bending the distal end of the extrusion.

The helical guide passages provided by lumens 26 and 28 should have a low coefficient of friction to reduce the loss in tension at the distal end, as tension is selectively applied to one of the tension members to bend the distal tip of the extrusion (i.e., of the flexible endoscope). For example, polytetrafluoroethylene, an example of which is sold by DuPont as TEFLON™, has a relatively low coefficient of friction (dynamic) of about 0.1 and would be a good exemplary choice material for the extrusion. Materials employed for the tension member should have properties such as high tensile strength, flexibility, toughness, and a low coefficient of friction. Exemplary materials suitable for the tension member include steel wire, fibers comprising long, highly oriented molecular chains of polyparaphenylene terephthalamide (an example of which is sold by DuPont as KEVLAR™ fibers), carbon fibers, and glass fibers. These materials can function very well as tension members in a flexible endoscope, particularly if coated with polytetrafluoroethylene or other low friction materials to ensure that they slide within lumens 26 and 28 with little friction.

In this exemplary embodiment of a flexible endoscope, the internal surface of central lumen 24 is bonded to the central optical fiber to transfer compression loading to the fiber. The bonding can be continuous along most of the length of the central lumen or at spaced-apart longitudinal intervals. One exemplary adhesive suitable for bonding the optical fiber to the extrusion within the central lumen is sold by Norton Performance Plastics Corporation of Wayne, N.J. as CHEMGRIP™, although other suitable adhesives can instead be employed. To ensure a good bond with the low friction material used for the extrusion (e.g., for example, a TEFLON™ material), it may be necessary to etch the material before the bonding step is attempted.

By bonding the extrusion to the optical fiber in this manner, and by employing a helical path 32 (i.e., helically extending lumens) for the tension members, the force applied to the tension members will not bend or distort a tether section of the flexible endoscope. The tether section is the portion of the flexible endoscope disposed between the distal tip and the proximal end of the flexible endoscope. Distortion of the tether section that would otherwise likely occur, as shown by the schematic illustrations in FIGS. 1A and 1B is avoided, since the helical lumens and the tension members within them correspond to the schematic illustration of FIGS. 2 and 3.

The extrusion also can include additional lumens 30 that extend longitudinally and helically, for providing access to the distal tip and to provide passages for one or more additional elements such as more optical fibers, wires (i.e., conductors), liquids, and gases. These additional elements can be employed in an exemplary flexible endoscope to enable functions such as: (1) performing biopsies; (2) improving visibility, for example, by circulating liquids and/or gases to an internal site proximate to the distal end of the flexible endoscope, or by employing suction to withdraw a sample of body fluid or simply to clear body fluid from a body passage through which the flexible endoscope is being advanced or from where it is be used to carry out other functions; and (3) administering therapies, e.g., drug delivery, light delivery, etc.

Near the distal end of the flexible endoscope, the tension members are attached within their respective lumens at an attachment point (as discussed below in connection with FIG. 7). These attachment points can be disposed as far as possible (radially) from the optical fiber (thereby creating a longer radially directed moment arm around the optical fiber (i.e., around the compression member), so that the tension from the tension member compresses the outer part of the extrusion adjacent to the tension member. With one side of the extrusion compressed, and the other opposite side relaxed, the distal tip of the endoscope will bend toward the tensioned side.

Figure 5:
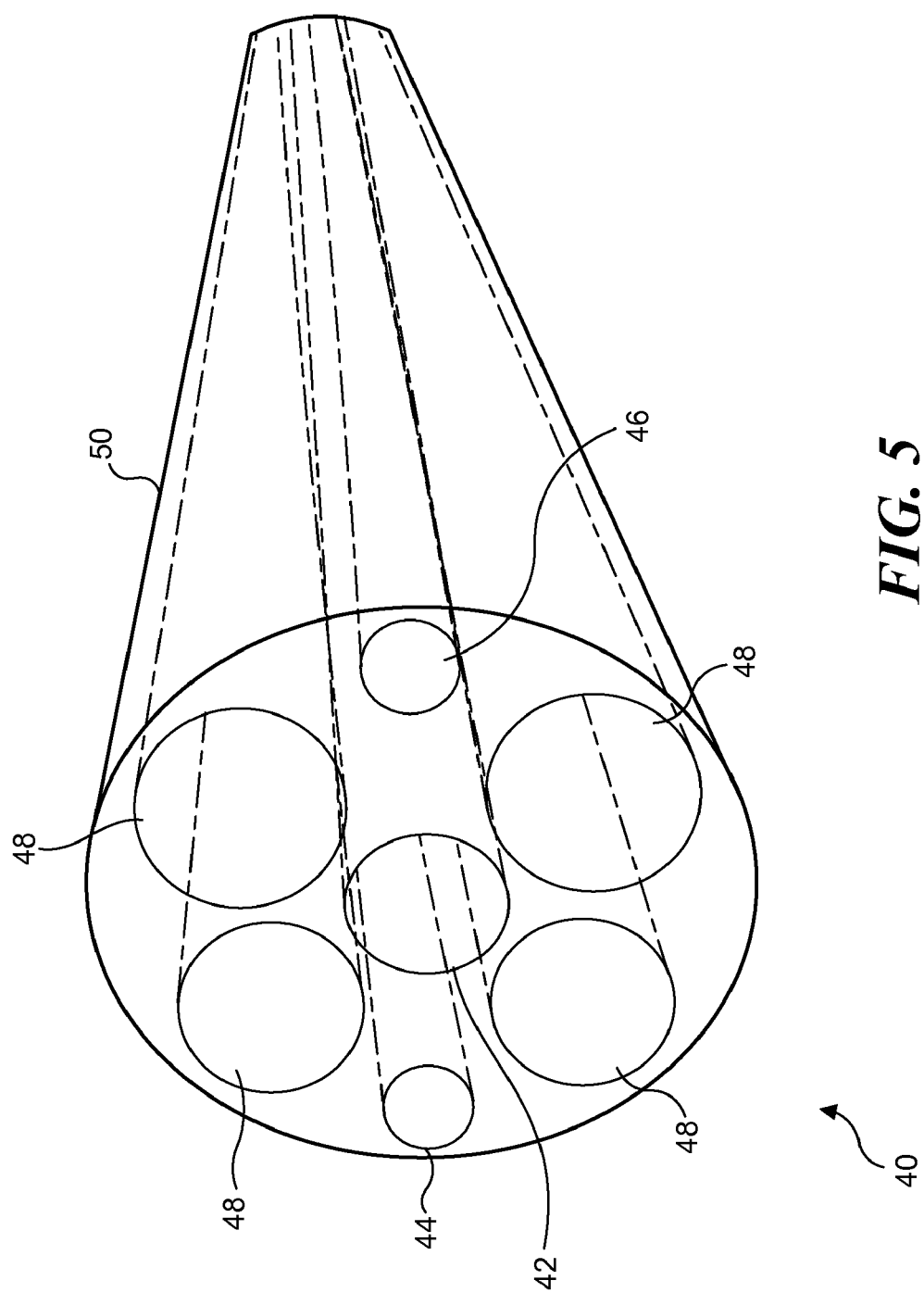
FIG. 5 is a cross-sectional perspective view of a portion of an extrusion of FIG. 4 that is actively bent and which has the two lumens spaced near the outer peripheral surface of the extrusion and the lumens do not wrap around the extrusion and are not bonded to the tension members.

FIG. 5 shows a flexible extrusion 50 for a distal part of an exemplary flexible endoscope 40 that is actively bent using tension members (not shown in this Figure). It should be noted that lumens 44 and 46, which serve as guide passages for the tension members, have been moved radially outward from a central lumen 42 and nearer to the perimeter of extrusion 50, compared to the position of lumens 24 and 26 in FIG. 4. Also, lumens 44 and 46 are straight and do not follow a helical path around central lumen 42. The optical fiber is not bonded to the internal surface of central lumen 42 in this exemplary distal portion of extrusion 50, which enables more of the flexible extrusion to compress, thus requiring less tension in the tension member that is being pulled to bend the distal end of the extrusion. As noted above, additional lumens 48 can optionally be included in extrusion 50 to provide a path for one or more other optical fibers, wire conductors, gases, liquids, or other components the user would like to enable to have access to the distal end of the extrusion, to perform various other functions, as discussed above.

The overall length of this flexible extrusion, and the tension in the tension member, determines the radius of curvature of the distal tip bend. Making the flexible extrusion shorter increases the tension required for a given angle of deflection, but also decreases the radius of curvature. Making the extrusion long decreases the tension required for a given angle of deflection of the distal tip, but also increases the radius of curvature.

The exemplary embodiment discussed above gives the capability to bend the tip back and forth (i.e., in either of two opposite directions) in one plane. A second plane for bending motion for the distal tip of a flexible endoscope can be achieved by adding a second pair of tension members that are disposed on diametrically opposite sides of the central lumen and on a line through the center of the central lumen that is rotated 90 degrees relative to a line through central lumen and the first pair of lumens used for the first pair of tension members. The first and second pair of tension members that extend through these four lumens provide a user the ability to bend the distal tip of the flexible endoscope relative to two orthogonal axes.

Figure 6:
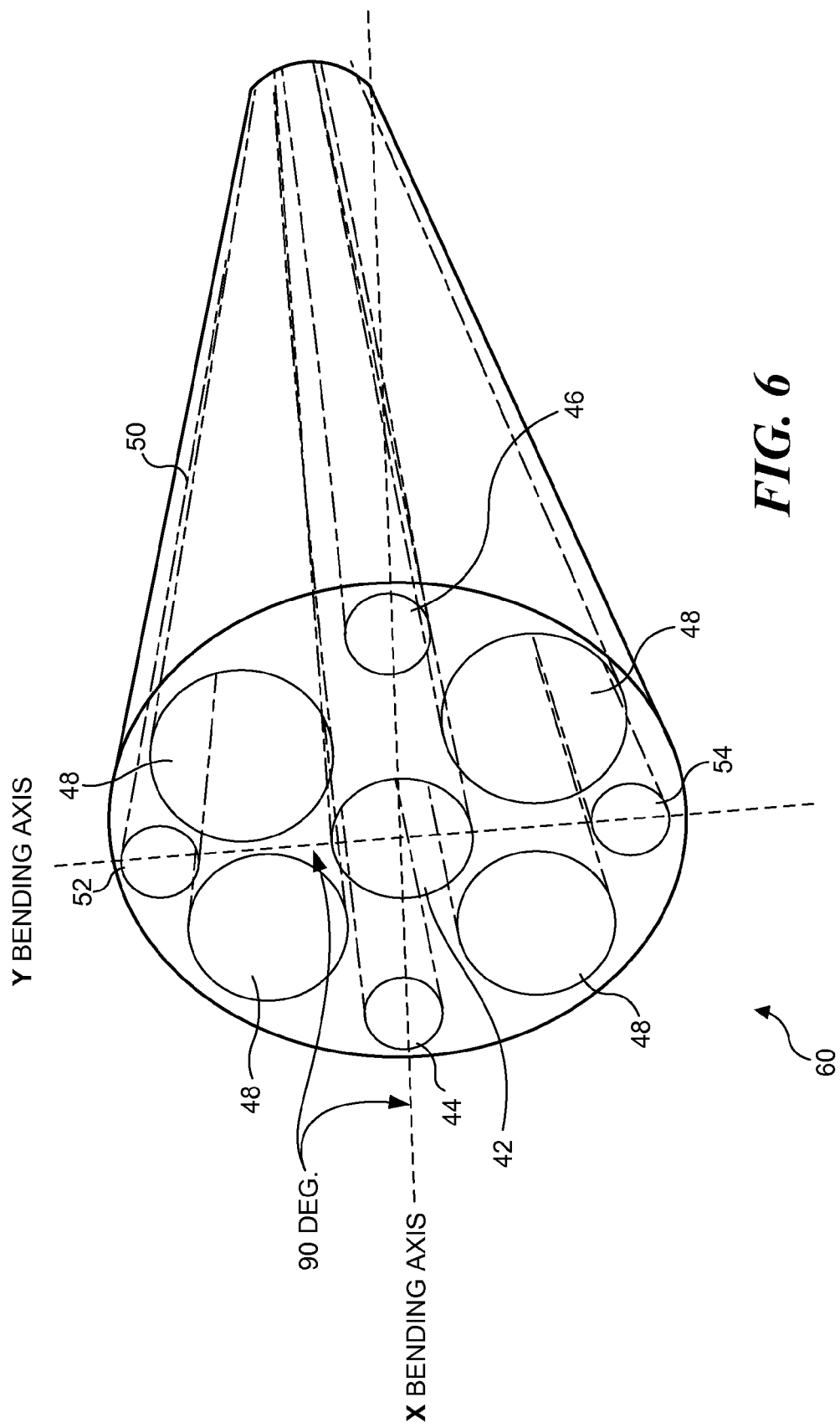
FIG. 6 illustrates the portion of an embodiment like the portion of FIG. 5, except that another pair of lumens are provided for tension members to enable the distal tip of the flexible endoscope to be bent in four different directions around two orthogonal axes instead of only in two opposite directions around a single axis.

FIG. 6 shows how the distal tip of a flexible endoscope 60 appears for an exemplary embodiment that a user is able to selectively bend relative to two orthogonal axes. The helical extrusion of the tether portion of this embodiment appears similar to the single bending axis exemplary embodiment shown in FIG. 4, but has two additional helical lumens 52 and 54 that serve as guides for the second pair of tension members. By applying different tensions to these four tension members, complete bending control of the distal tip can be achieved, which is a very important capability in long, very small diameter flexible endoscopes. Present practice is to enable an endoscope distal tip to bend in only one direction, and when necessary to look in a different direction, the endoscope is physically twisted. However, when employing a very small diameter, long flexible endoscope, attempting to twist the shaft of the endoscope can generate a sufficiently large torque to damage the endoscope. Accordingly, it will generally be preferable to employ a flexible endoscope that includes two pairs of tension members disposed at cardinal points around the central lumen, so that complete bending control of the distal tip in any direction can be accomplished.

Detailed Description of Distal End of Exemplary Flexible Endoscope

Figure 7:
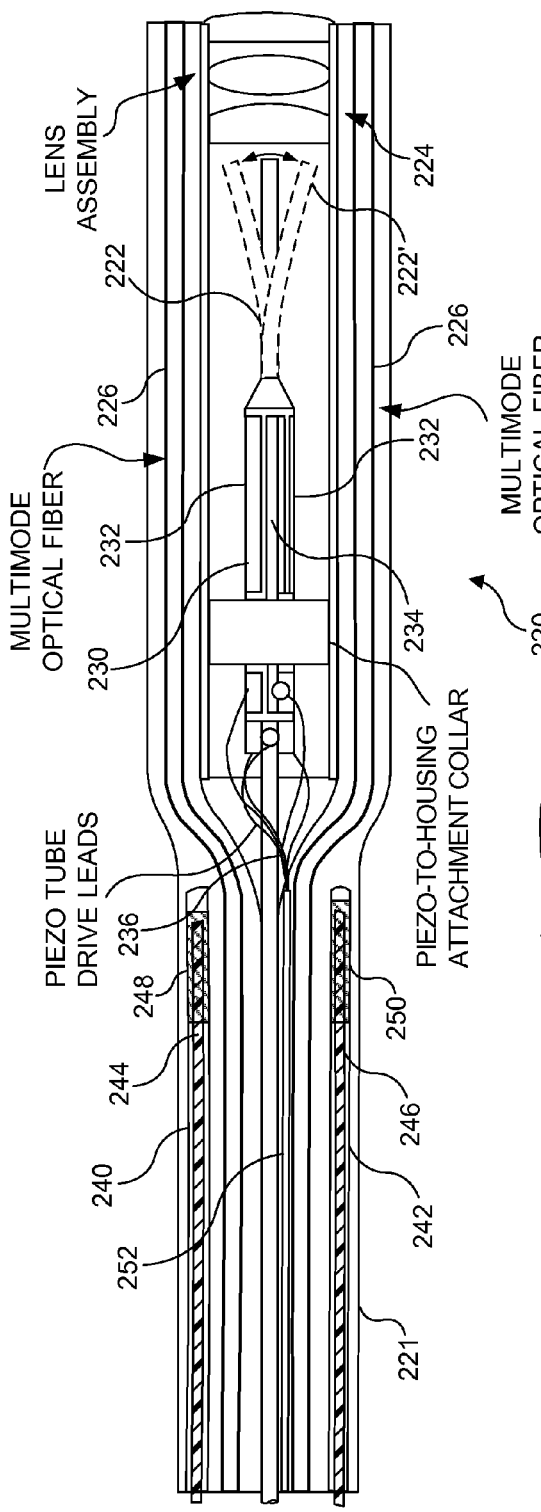
FIG. 7 is a schematic cross-sectional view of a flexible endoscope with a scanning optical fiber and helically extending tension members (only two shown)

The distal end of exemplary flexible endoscope 220 shown in FIG. 7 includes a scanning optical fiber 222, which is driven to scan in a desired scan pattern at or near its resonant frequency, as indicated by its positions in phantom view, e.g., at reference numeral 222'. A lens assembly 224 is provided at the distal end of flexible endoscope 220 and is employed for focusing the light exiting the scanning optical fiber 222 onto a site. Two or more multimode optical fibers 226 are disposed peripherally around scanning optical fiber 222, within a flexible extrusion 221, and are used for conveying reflected light to one or more photodetectors (not shown) that are disposed at the proximal end of the flexible endoscope. (Alternatively, in another exemplary embodiment that is not shown, photodetectors can be disposed at the distal end of the flexible endoscope and used to directly receive the reflected light, producing signals that are conveyed through signal leads provided instead of multimode optical fibers 226.)

Scanning optical fiber 222 is driven in a desired pattern by a piezoelectric tube actuator 230 relative to two orthogonal axes, in response to drive signals supplied to electrodes 232 and 234 through electrical leads 236, which extend proximally through a lumen 252 within flexible endoscope 220. A single-axis (linear) scan pattern can, for example, be generated by applying voltage to one electrode 232 or to opposing electrodes 234 of piezoelectric tube actuator 230. By applying an oscillating periodic voltage (e.g., a sine wave) having a frequency at or near the mechanical resonant frequency of the base-excited scanning optical fiber cantilever to the actuator through electrical leads 236, the amplitude of the tip motion can be mechanically amplified due to the mechanical resonance of the scanning optical fiber cantilever. Furthermore, for example, the concurrent application of a second periodic voltage (a cosine wave) to electrodes 234 (which are orthogonal to electrodes 232) on the actuator, at the same or slightly different resonant frequency, causes the resonating optical fiber tip to move in an elliptical scanning pattern.

A signal useful for producing an image is generated by the optical fiber scanner shown in FIG. 7, by directing the light emitted from scanning optical fiber 222 onto a region at an internal site. Light transmitted toward the region by the scanning optical fiber cantilever is focused using imaging lenses 224. Typically, the imaging lenses focus the light, directing it to a scanned portion of the internal site as the scanning optical fiber resonantly scans the site with either a linear (one-dimensional), or with spiral, elliptical, or other two-dimensional patterns. By varying the amplitude of the voltages applied to the actuator during the elliptical scan, a two-dimensional (2-D) space-filling scanning pattern is formed. Multimode optical fibers 226 that surround the scanning optical fiber receive the light that is reflected from tissue at the internal site, and this light is used for generating the 2-D image or for evaluating parameters of the tissue. Typically, multimode optical fibers 226 convey the received light to one or more detectors (not shown) for producing signals used for imaging the site or for other purposes, such as diagnostic evaluation. It should be emphasized that in this exemplary embodiment, scanning optical fiber 222 also serves as a compression member to facilitate bending the distal end of the flexible endoscope, as illustrated and discussed below in connection with FIG. 8.

Proximal of piezoelectric tube actuator 230, flexible extrusion 221 includes lumens 240 and 242 disposed on diametrically opposite sides of the scanning optical fiber and the lumen through which it extends. Within lumens 240 and 242 are respectively disposed tension members 244 and 246. The distal end of tension member 244 is coupled to flexible extrusion 221 by an adhesive patch 248. Similarly, the distal end of tension member 246 is coupled to the extrusion by an adhesive patch 250. The adhesive patches can be a thermally or chemically set adhesive, or other suitable type of adhesive. For example, a thermal adhesive may melt when heated and solidify when cooled, to anchor the distal ends of the tension members at attachment points within their respective lumens. These attachment points are proximate the distal end of extrusion 221.

For purposes of clarity, FIG. 7 does not show two additional lumens, which are optionally included in extrusion 221 to enable bending of the distal end of flexible endoscope 220 in a second plane that is orthogonal to the plane in which tension members 244 and 246 can bend the distal tip. Providing the second pair of lumens and second pair of tension members enables a user to selectively bend the distal tip of the flexible endoscope in any desired direction by applying appropriate tension to one or more of the four tension members having distal ends connected to the extrusion at cardinal attachment points around the scanning optical fiber.

In the tether portion of the flexible endoscope (not shown in this Figure) that begins a few centimeters proximal of the distal portion of flexible endoscope 220 of FIG. 7, the lumens disposed around the scanning optical fiber twist in a helical spiral, generally as shown for exemplary flexible endoscope 20 in FIG. 4. The helical twist can be formed in extrusion 221 by heating the flexible extrusion sufficiently to soften it. The tether portion of the extrusion is then twisted at its proximal end sufficiently to create the desired helical spiral of the lumens that serve as guides for the tension members (and also, the helical spiral of the other lumens disposed around the central lumen). The scanning optical fiber is then bonded to extrusion 221 within the tether portion of the flexible endoscope, either continuously along its length in that portion or at longitudinally spaced-apart points. Bonding the scanning optical fiber to the extrusion thus sets and maintains the helical twist of these surrounding lumens after the extrusion cools.

Figure 8:
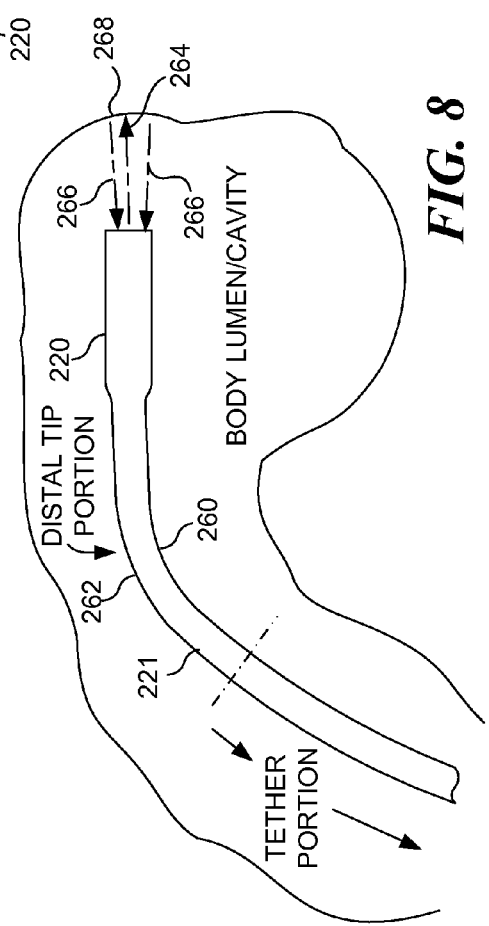
FIG. 8 is a schematic view of an internal lumen/body cavity in which the flexible endoscope of FIG. 7 is illustrated, showing how the distal tip of the flexible endoscope is bent in a desired direction.

FIG. 8 illustrates how a flexible endoscope can be selectively bent by applying tension to tension member 246 (which is close to an inside radius 260 of the bend, compared to tension member 244 that is close to an outside radius 262 of the bend). By bending the distal end of flexible endoscope 220, it is possible to more readily advance it through circuitous body passages to a desired body lumen/cavity. By bending the distal tip of the flexible endoscope as desired, the distal end of flexible endoscope 220 can be positioned adjacent to tissue 268 that is to be imaged (or treated with an optical therapy delivered through optical fibers that are not shown). The scanning optical fiber can then emit illumination light 264 directed toward tissue 268, and the multimode optical fibers within the flexible endoscope can receive reflected light 266 from the tissue in a patient's body.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A flexible endoscope having a distal tip that can be selectively bent, comprising:
   (a) a flexible extrusion that is elongate, extending between a proximal end and a distal end and having a plurality of lumens formed therein, at least two lumens of the plurality of lumens being disposed on diametrically opposite sides of, and radially outward of a central lumen within the flexible extrusion, where the central lumen is centered about and extends longitudinally along a centerline of the flexible extrusion;
   (b) at least a pair of tension members, each extending proximally through a different one of the plurality of lumens from an attachment point where the tension member is connected to the flexible extrusion, each attachment point being disposed adjacent to the distal tip of the flexible extrusion, the tension members being free to slide longitudinally within the lumens proximal of the attachment points; and
   (c) an optical fiber that conveys light disposed within the central lumen and bonded to a portion of an internal surface of the central lumen within the flexible extrusion proximal of a distal portion of the extrusion, the optical fiber being configured as a compression member and disposed between the tension members, so that when tension is applied to a first tension member relative to the optical fiber, the distal tip of the flexible endoscope is bent in a first direction, and when tension is applied to a second tension member that is disposed generally diametrically opposite the first tension member, the flexible endoscope is bent in a second direction that is opposite to the first direction, enabling the distal tip of the flexible endoscope to be selectively caused to bend in at least two generally opposite directions, wherein the at least two lumens extend helically around the central lumen in a portion of the flexible endoscope that is proximal of a distal tip portion of the flexible endoscope.

2. The flexible endoscope of claim 1, wherein the at least the two lumens are disposed relatively radially closer to the central lumen in a portion of the flexible endoscope that is proximal of a distal tip portion, than in the distal tip portion of the flexible endoscope.

3. The flexible endoscope of claim 1, wherein the flexible extrusion is formed of a material selected to have a relatively low coefficient of friction, to enable the at least the pair of tension members to slide easily within the lumens in which the tension members are disposed.

4. The flexible endoscope of claim 3, wherein the material comprises polytetrafluoroethylene.

5. The flexible endoscope of claim 1, wherein each of the at least the pair of tension members are formed of one or more materials selected to have defined characteristics, including a relatively high tensile strength, flexibility, toughness, and a low coefficient of friction.

6. The flexible endoscope of claim 5, wherein the at least the pair of tension members comprises a material selected from the group consisting of:
   (a) steel wires;
   (b) fibers comprising long, highly oriented molecular chains of poly-paraphenyleneterephthalamide;
   (c) carbon fibers; and
   (d) glass fibers.

7. The flexible endoscope of claim 1, wherein the plurality of lumens formed in the flexible extrusion includes at least one lumen not used in connection with bending the distal tip, adapted to pass at least one element selected from the group consisting of:
   (a) one or more optical fibers;
   (b) one or more wires;
   (c) one or more liquids; and
   (d) one or more gases.

8. The flexible endoscope of claim 7, wherein the at least one element that can be passed through the at least one lumen not used in connection with bending the distal tip, is used for at least one function selected from the group consisting of:
   (a) performing a biopsy;
   (b) modifying a visibility in a region of a patient's body in which the flexible endoscope is adapted to be inserted; and
   (c) rendering a therapy to a portion of a patient's body.

9. The flexible endoscope of claim 1, wherein the plurality of lumens comprises a first pair of lumens, each of which is disposed on diametrically opposite sides of the central lumen, and a second pair of lumens, each of which is disposed on diametrically opposite sides of the central lumen, but oriented orthogonally relative to the first pair of lumens, so that a line extending through a center of the central lumen between the lumens of the first pair is generally perpendicular to a line extending through the center of the central lumen between the lumens of the second pair, and wherein the at least the pair of tension members include a first pair of tension members, each of which is disposed in a different one of the first pair of lumens, and a second pair of tension members, each of which is disposed in a different one of the second pair of lumens, the first pair of tension members being used to bend the distal end of the flexible endoscope in a first plane, and the second pair of tension members being used to bend the distal end of the flexible endoscope in a second plane that is orthogonal to the first plane.

10. A flexible endoscope having a distal tip that can be selectively caused to bend in different directions, comprising:
    (a) a flexible extrusion that is elongate, extending between a proximal end and a distal end and having:
       (i) a central lumen that extends longitudinally along and centered about a centerline of the flexible extrusion; and
       (ii) a plurality of helical lumens formed within the flexible extrusion, spaced-apart from and around the central lumen, wherein the plurality of helical lumens are at least disposed on diametrically opposite sides of, and radially outward of the central lumen;
    (b) at least a pair of tension members, each extending proximally through a different one of the plurality of helical lumens and being connected to the flexible extrusion at an attachment point, each attachment point being disposed adjacent to the distal tip of the flexible extrusion, the tension members being free to slide longitudinally within the helical lumens proximal of the attachment points; and
    (c) an optical fiber disposed within the central lumen and connected to a portion of an internal surface of the central lumen within the flexible extrusion, the optical fiber conveying light and being configured as a compression member and disposed between the tension members, so that when tension is applied to a first tension member relative to the optical fiber, the distal tip of the flexible endoscope is bent in a first direction, and when tension is applied to a second tension member that is disposed generally diametrically opposite the first tension member, the flexible endoscope is bent in a second direction that is opposite to the first direction, enabling the distal tip of the flexible endoscope to be selectively caused to bend in at least two opposite directions.

11. The flexible endoscope of claim 10, wherein the at plurality of helical lumens comprises a first pair of helical lumens disposed on opposite sides of the central lumen, and a second pair of helical lumens disposed on opposite sides of the central lumen, so that the helical lumens are spaced apart by about 90 degrees, and wherein the at least the pair of tension members include a first pair of tension members, each of which is disposed in a different one of the first pair of helical lumens, and a second pair of tension members, each of which is disposed in a different one of the second pair of helical lumens, the first pair of tension members being used to bend the distal end of the flexible endoscope in a first plane, and the second pair of tension members being used to bend the distal end of the flexible endoscope in a second plane that is generally orthogonal to the first plane.

12. The flexible endoscope of claim 10, wherein the at least the pair of tension members comprises a non-metallic material selected for a characteristic high tensile strength.

13. The flexible endoscope of claim 12, wherein the non-metallic material is selected from the group consisting of:
    (a) fibers comprising long, highly oriented molecular chains of poly-paraphenyleneterephthalamide;
    (b) carbon fibers; and
    (c) glass fibers.

14. The flexible endoscope of claim 10, wherein tension members disposed on opposite sides of the central lumen are spaced diametrically further apart proximate the distal tip, than in a tether portion of the flexible endoscope that extends from about the distal tip to the proximal end of the flexible endoscope.

15. The flexible endoscope of claim 10, wherein the flexible extrusion is formed of a material selected for a characteristic low coefficient of friction, so that each tension member is able to readily slide within the helical lumen through which the tension member passes.

16. The flexible endoscope of claim 15, wherein the material comprises polytetrafluoroethylene.

17. A flexible endoscope having a distal tip that can be selectively caused to bend in different directions, comprising:
    (a) a flexible extrusion that is elongate, extending between a proximal end and a distal end and having a plurality of lumens formed therein, at least two lumens of the plurality of lumens being disposed on opposite sides of, and radially outward of a central lumen that extends longitudinally along and centered about a centerline of the flexible extrusion;
    (b) at least a pair of tension members, each extending proximally through a different one of the plurality of lumens from an attachment point where the tension member is connected to the flexible extrusion, each attachment point being disposed adjacent to the distal tip of the flexible extrusion, the tension members being formed of a non-metallic material that is able to slide within the lumens proximal of the attachment points; and (c) a compression member comprising at least a portion of an optical fiber, disposed within the central lumen and between the tension members, and bonded to a portion of an internal surface of the central lumen within the flexible extrusion, so that when tension is applied to a first tension member relative to the compression member, the distal tip of the flexible endoscope is bent in a first direction, and when tension is applied to a second tension member that is disposed on an opposite side of the compression member from the first tension member, the flexible endoscope is bent in a second direction that is opposite to the first direction, enabling the distal tip of the flexible endoscope to be selectively caused to bend in at least two opposite directions, wherein the plurality of lumens form a helix around the central lumen, so that when the distal tip of the flexible endoscope is caused to bend, relative lengths of tension members on an inner side of a bend in the distal tip and on an outer side of the bend, generally do not change.

18. The flexible endoscope of claim 17, wherein the compression member comprises an optical fiber that also conveys light through the central lumen, between distal and proximal ends of the flexible endoscope.

19. The flexible endoscope of claim 17, wherein at least one component other than a tension member is conveyed through at least one of the plurality of lumens, the at least one component being used to carry out at least one function other than causing the distal tip to bend.

20. The flexible endoscope of claim 19, wherein the at least one different function comprises one or more functions selected from the group consisting of:
   (a) performing a biopsy;
   (b) improving visibility at a site within a patient's body at which the distal tip of the flexible endoscope is disposed; and
   (c) rendering a therapy to a site within a patient's body.

21. The flexible endoscope of claim 17, wherein the flexible extrusion is formed of a polytetrafluoroethylene material having a characteristic low coefficient of friction, so that each tension member is able to readily slide within the lumen through which the tension member extends.

* * * * *